United States Patent
Scarberry et al.

(10) Patent No.: US 6,397,847 B1
(45) Date of Patent: Jun. 4, 2002

(54) CUSTOMIZABLE SEAL, MASK WITH CUSTOMIZABLE SEAL AND METHOD OF USING SUCH A SEAL

(75) Inventors: Eugene N. Scarberry, Trafford, PA (US); Ronald E. White, Sharpsburg; Benedict R. McElroy, Boonsboro, both of MD (US)

(73) Assignee: Respironics, Inc., Pittsburgh, PA (US)

( * ) Notice: Subject to any disclaimer, the term of this patent is extended or adjusted under 35 U.S.C. 154(b) by 0 days.

(21) Appl. No.: 09/388,326

(22) Filed: Sep. 1, 1999

Related U.S. Application Data

(63) Continuation of application No. 08/832,267, filed on Apr. 3, 1997, now Pat. No. 5,884,624, which is a continuation of application No. 08/525,404, filed on Sep. 9, 1995, now Pat. No. 5,647,357.
(60) Provisional application No. 60/103,091, filed on Oct. 5, 1998.

(51) Int. Cl.[7] ............................................. A62B 18/08
(52) U.S. Cl. ........................... 128/206.24; 128/206.23; 128/206.21; 128/206.25; 128/206.14; 128/848; 2/430
(58) Field of Search ..................... 128/206.24, 206.23, 128/206.31, 206.25, 206.14, 201.18, 848, 846; 2/430

(56) References Cited

U.S. PATENT DOCUMENTS

| | | |
|---|---|---|
| 2,254,854 A | 9/1941 | O'Connell |
| 2,625,155 A | 1/1953 | Engelder |
| 2,837,090 A | 6/1958 | Bloom et al. |
| 2,917,045 A | 12/1959 | Schildknecht et al. |
| 2,931,356 A | 4/1960 | Hermann et al. |
| 4,369,284 A | 1/1983 | Chen |
| 4,665,570 A | 5/1987 | Davis |
| 5,181,506 A | 1/1993 | Tardiff, Jr. et al. |
| 5,334,646 A | 8/1994 | Chen |
| 5,343,878 A | 9/1994 | Scarberry et al. |
| 5,647,357 A | 7/1997 | Barnett et al. |
| 5,662,101 A | 9/1997 | Ogden et al. |
| 5,884,624 A | 3/1999 | Barnett et al. |

FOREIGN PATENT DOCUMENTS

| | | |
|---|---|---|
| CA | 618807 | 4/1961 |
| WO | WO 99/58198 | 11/1999 |

OTHER PUBLICATIONS

S.F.C. Stewart et al., "Wheelchair Cushion Effect on Skin Temperature, Heat Flux, and Relative Humidity," Arch Phys Med Rehabil, vol. 61, May 1980, 229–233.

*Primary Examiner*—John G. Weiss
*Assistant Examiner*—Darwin Erezo
(74) *Attorney, Agent, or Firm*—Michael W. Haas

(57) ABSTRACT

A seal and a mask having a seal adapted for confronting engagement with a surface of a user to form an interface therewith. The seal includes a first portion defined by a gel substance and a second portion associated with the first portion. The second portion includes a selectively formable substance adapted to be molded from a first pattern into a second pattern and to retain the second pattern responsive to being so molded. The seal and mask having the seal is tailored to patient by causing the formable portion of the seal to be placed in a malleable state, applying the seal to the patient while the formable portion is in the malleable state, and causing the formable portion to be placed in a fixed state to retain a shape generally conforming to the portion of the patient underlying the seal.

22 Claims, 9 Drawing Sheets

CUSTOMIZABLE SEAL, MASK WITH CUSTOMIZABLE SEAL AND METHOD OF USING SUCH A SEAL

CROSS REFERENCE TO RELATED APPLICATIONS

This application claims priority under 35 U.S.C. §119 from Provisional U.S. Patent Application No. 60/103,091 filed Oct. 5, 1998, and is a continuation of U.S. patent application Ser. No. 08/832,267 filed Apr. 3, 1997, which issued as U.S. Pat. No. 5,884,624 on Mar. 23, 1999, which is a Continuation of U.S. patent application Ser. No. 08/525,404 filed Sep. 9, 1995, which issued as U.S. Pat. No. 5,647,357 on Jul. 15, 1997.

BACKGROUND OF THE INVENTION

1. Field of the Invention

The present invention pertains to a customizable seal that contacts a portion of a patient to provide a comfortable and customizable interface between an external device, such as a respiratory mask, and the patient. The present invention also pertains to a respiratory mask having such a customizable seal and to a method of interfacing a patient with an external device, such as a respiratory mask, using such a seal.

2. Description of the Related Art

A variety of respiratory masks are known having a flexible seal that covers the areas surrounding the nose and/or mouth of a human user and that are designed to create a continuous seal against the user's face. Because of the sealing effect created, gases can be provided at a positive pressure within the mask for consumption by the user. The uses for such masks range from high altitude breathing (aviation applications), swimming, mining and fire fighting applications and various medical diagnostic and therapeutic applications.

One requisite of many of these masks, particularly medical respiratory masks is that they provide an effective seal against the user's face to prevent leakage of the gas being supplied. Commonly, in conventional mask configurations, a good mask-to-face seal has been attained in many instances only with considerable discomfort for the user. This problem is most crucial in those applications, especially medical applications, which require the user to wear the mask continuously for hours or perhaps even days. In such situations, the user will not tolerate the mask for long durations and optimum therapeutic or diagnostic objectives will not be achieved, or will be achieved with great difficulty and considerable user discomfort.

Several types of respiratory masks for the types of applications mentioned above are known. Perhaps the most common type of mask incorporates a smooth sealing surface extending around the periphery of the mask and exhibiting a generally uniform, i.e., predetermined or fixed, seal surface contour that is intended to be effective to seal against the user's face when force is applied to the mask with the sealing surface in confronting engagement with the user's face. The sealing surface typically consists of an air or fluid filled cushion, or it may simply be a molded or formed surface of a resilient seal element made of an elastomer such as plastic, rubber, silicone, vinyl or foam.

Such masks have performed well when the fit is good between the contours of the seal surface and the corresponding contours of the user's face. This may occur, for example, if the contours of the user's face happen to match well with the predetermined contours of the seal. However, if the seal fit is not good, there will be gaps in the seal-to-face interface resulting in gas leaking from the mask at the gaps. Excessive force will be required to compress the seal member to close the gaps and attain a satisfactory seal in those areas where the gaps occur. Such excessive force is unacceptable because it produces high pressure points elsewhere on the face of the user where the mask seal contour is forcibly deformed against the face to conform to the user's facial contours. This will produce considerable user discomfort and possible skin irritation and breakdown anywhere the applied force exceeds the local perfusion pressure, which is the pressure that is sufficient to cut off surface blood flow. Ideally, contact forces should be limited between the mask and the user's face to avoid exceeding the local perfusion pressure, even at points where the mask seal must deform considerably.

The problem of seal contact force exceeding desirable limits is even more pronounced when the positive pressure of the gas being supplied is relatively high or is cyclical to relatively high levels. Because the mask seals by virtue of confronting contact between the mask seal and the user's face, the mask must be held against the face with a force sufficient to seal against leakage of the peak pressure of the supplied gas. Thus, for conventional masks, when the supply pressure is high, headstraps or other mask restraints must be relatively tightly fastened. This produces high localized pressure on the face, not only in the zone of the mask seal, but at various locations along the extent of the retention straps as well. This, too, will result in discomfort for the user after only a brief time. Even in the absence of excessive localized pressure points, the tight mask and headstraps may become extremely uncomfortable, and user discomfort may well cause discontinued cooperation with the treatment regimen. Examples of respiratory masks possessing continuous cushion sealing characteristics of the type just described are provided in U.S. Pat. Nos. 2,254,854 and 2,931,356.

U.S. Pat. No. 5,181,506 describes a protective gas mask for military applications. The mask includes a three-layer face piece, the central layer of which is a thick layer of relatively stiff material having preformed V-shaped channels. The channels are "overfilled" with a gel or both gel and compressed air to create bulges in an inner face-contacting layer that are adapted to seal against the contours of a user's face. The inherent stiffness of the central layer in combination with the structural rigidity provided by the V-shaped channels, especially when overfilled with gel/air, results in a comparatively unyielding facial seal. Indeed, the mask is deployed in combination with a tightly fitting hood in order to draw the face piece firmly against the user's head to generate the desired facial seal. As will be appreciated, the comfort afforded such a construction is quite limited and certainly not appropriate for those applications, such as respiratory therapy situations, where a user must occasionally wear a mask for prolonged periods of time.

Several classes of cushion materials, including gels and foams, were analyzed in a study by S. F. C. Stewart, V. Palmieri and G. V. B. Cochran, *Arch. Phys. Med. Rehabil.*, Vol. 61, (May 1980). That study compared the relative advantages and disadvantages of such cushion materials when used as wheelchair cushions, specifically the effects of such materials on skin temperature, heat flux and relative humidity at the skin-cushion interface. Each of these factors, along with applied pressure in excess of local perfusion pressure, has been identified as a contributor to breakdown of skin tissue at the skin-cushion interface.

In that study, foam cushions were reported to increase skin temperatures by several degrees after a few hours of use. This was suggested to be a result of the comparatively low heat flux characteristics of foam materials. That is, the foam materials and the air entrapped within them tend to be poor conductors of heat. Conversely, gel pads, as a group, showed a considerably higher heat flux than foam, sufficient, in fact, to maintain skin temperatures relatively constant after several hours of use. The sole benefit of foam versus gel reported in the study was that foams produced lesser relative humidity than gels at the skin-cushion interface. This was attributed to the open cell structure of the foams which provide a pathway through which moisture can diffuse. This seeming advantage is somewhat problematic, however, in that open cell foam tends to promote bacteria growth when exposed to perspiration. Bacteria, in turn, contaminates the foam thereby considerably hindering its useful service life.

These and other detrimental characteristics have been observed as well in the foam-type respiratory mask seals discussed above. Hence, apart from generally failing to provide optimum sealing with respect to a user's face, the inherent qualities of foam mask seals have been linked to skin irritation and breakdown, particularly at some of the more prominent facial contours, such as the cheek bones and bridge of the nose.

Moreover, whether air, fluid or, in the case of U.S. Pat. No. 5,181,506, gel filled, or whether formed as an elastomer such as foam, plastic, rubber, silicone and the like, the resiliency or recoil characteristics of presently available cushion type respiratory mask seals have not been well suited to form an effective seal with the topography of the user's face in the absence of considerable headstrap tensile forces.

One method to reduce the existence of gaps at the mask-to-face interface is to customize the seal so that it conforms to the fine contours of the patient's face. This can be thought of as a micro-customization of the seal because the goal of the customization is to match the seal to the specific external features of the user's face, i.e., the contours created by the soft tissue of the patient. For example, if the user has an unusually deep crease in his or her face, a micro-customized mask has a user interface surface that matches this deep crease, thereby preventing a gap from existing at the crease. In short, a micro-customized seal is tailored to conform to the contours of the soft surface tissue of the patient.

Various techniques have been proposed for micro-customizing a seal, such as the seal on a face mask. It is known, for example, to provide a micro-customized seal by making an impression or cast of the patient's face. The cast is then used as a form to produce a fully customized mask specifically tailored to match that patient's face. This technique, however, is time consuming and costly, and, therefore, is not well suited for conventional, large-scale manufacturing processes.

The present inventor also discovered that, contrary to expected results, a satisfactory seal may not result from a micro-customized mask. It is believed that a relatively detailed micro-customized mask, closely matching the detailed contours of the soft tissue at the surface of a patient, does not provide a satisfactory seal because changes in seal position and/or changes in the soft tissue of the patient may result in new gaps being created between the seal and the patient. For this reason, a mask that has a micro-customized seal made from the above-described casting process, because it is specifically designed to match the contours in the soft tissue of the patient's face at the time the cast was made, typically does not have the ability, or has only a limited ability, to change its shape in the event of changes in the patient's shape or shifts in the mask position. This disadvantage is especially pronounced if the mask having such a micro-customized seal is used in situations where the patient is likely to move and/or in situations where the mask is likely to be jostled, such as during sleep.

It is also known to contour the patient-contacting surface of the mask to match the general facial contours of the patient. This can be thought of as a macro-customization because the goal of customization is not to match the seal to the detailed external features of the user defined by the external soft tissues, but to match the seal to the general shape of the user, such as the underlying bone structure. Macro-customization provides an advantage over micro-customization in that there is less of a chance that changes in the patient's soft tissue or slight shifts in the seal will result in gaps being created. Also, a macro-customized seal provides a more effective seal than a micro-customized seal in situations where there may be differences between the contours of the underlying bone structure and the overlying soft tissue. For example, if there is a protruding bone that is not apparent because the protrusion is masked by soft tissue, a macro-customized seal will conform to the protruding bone structure, thereby minimizing the chances of leaks existing at a site near the protruding bone.

One technique for providing a macro-customized seal on a respiratory mask is to provide a variety of different masks having a variety of differently shaped seals. The user would use the mask having the seal that most closely matches the facial structure of that user. For example, several masks having different sized nose bridge arches can be made available to the user, with the user selecting the mask having the nose bridge arch size that most closely matches his or her nose. This type of mask provides some degree of customization, as opposed, for example, to a flat surface, for the mask-to-patient interface. However, because this macro-customized, i.e., off the shelf, mask is not specifically customized to match the facial features of a specific user, it often does not permit a sufficient degree of customization to account for facial contours specific to each patient. For example, for patients with unusual facial features, off the shelf macro-customized masks typically do not provide a satisfactory seal and can result in pressure points being created as the patient attempts to close these gaps with increased strapping force.

Macro-customization of a respiratory mask facial seal can also be accomplished by measuring the general facial features of the patient and producing a seal that matches these general features. This macro-customization process, however, suffers from the same disadvantages discussed above with respect to the micro-customization process. Namely, it is time consuming, uneconomical and inefficient to attempt to mass produce such specifically tailored macro-customized masks.

Macro-customization also suffers from a disadvantage in that leaks resulting from the physical characteristics of the soft tissue of the patient are not minimized. For example, if there is a deep crease in the soft tissue, a macro-customized seal is generally not as prone to reducing leaks at the crease as a micro-customized seal. Instead, the user will typically attempt to minimize such leaks by increasing the strapping force, thereby creating the problems of high localized pressure on the surface of the patient.

SUMMARY OF THE INVENTION

Accordingly, it is an object of the present invention to provide a customizable seal adapted for confronting engagement with a surface of a user to form a sealed interface therewith that overcomes the shortcomings of conventional seal techniques. This object is achieved, according to one embodiment of the present invention, by providing a seal having a first portion defined by a gel substance and a second portion associated with the first portion and including a selectively formable substance adapted to be molded from a first pattern into a second pattern and to retain the second pattern responsive to being so molded. The first portion of the seal has the effect of providing a micro-customization of the seal in that the seal readily conforms to match the external contours of the user, such as those features defined in a patient's soft tissues. The second portion of the seal has the effect of providing a macro-customization in that it can be molded to match the general features, such as the underlying bone structure, of the patient.

The present inventor discovered that headstrap tensile forces and, therefore, the compressive forces exerted by the mask against a user's face, can be reduced substantially with respect to existing cushion-type respiratory masks when the first portion of the seal in a respiratory facial mask is fabricated from materials, such as a gel substance, having recoil characteristics analogous to that of human fat. The first portion of the seal behaves much like natural biological tissue and tends to conform naturally to the detailed contours of the user's face under the influence of very low headstrap forces. Therefore, the first portion of the seal provides the advantages associated with micro-customization in that the seal can conform to the detailed features of the user's skin.

The present inventor also discovered that, in addition to their other aforementioned advantages, gel substances can be produced that simulate the recoil properties of human fat tissue. In one embodiment, the gel substance is, for example, a viscoelastic polyurethane polymer possessing a resiliency characteristic corresponding to that of human fat tissue yet having a recoil property such that the seal returns back to substantially its original shape after being stressed. In a further embodiment, a protective covering is provided over an exterior surface of the gel substance. In the absence of such a covering, the inherent tacky quality of the gel substance serves to enhance adhesion of the facial seal to the user's skin. Alternatively, if tackiness is not desired, the surface of the annular member may be covered with a coating of powdered talc, silicone or similar biocompatible material. Most preferably, however, an exposed portion of the gel substance is encapsulated in a thin, pliable, membranous covering to enhance the durability and washability of the facial seal.

Because the portion of the facial seal that contacts the user simulates the recoil characteristics of human fat tissue, the user experiences the sensation of a natural substance against his or her skin when an external device, such as a mask, having such a seal is donned. Furthermore, because the seal includes a second portion that can be molded from a first pattern into a second pattern and, thereafter, retains the second pattern, a respiratory mask having such a seal can be customized to match the general facial characteristics of the user. The second portion of the seal provides the advantages associated with macro-customization in that the seal conforms to the general features of the user. Consequently, an external device, such as a mask, provided with such a customizable seal can be comfortably urged into continuous sealing engagement with a user's face with less headstrap tension than other masks heretofore known in the art. Furthermore, the fat-like qualities of the gel substance in the first portion of the seal allow the gel to effectively fill gaps on the surface of the user and mold to other facial contours, thereby minimizing leakage of pressurized gas supplied to the mask. The gel substance also serves to efficiently dissipate heat while resisting the bacteria growth associated with foam type mask seals.

It is a further object of the present invention to provide a respiratory mask using a customizable seal described above. This object is achieved by providing a respiratory mask that includes a relatively rigid mask body having a first opening and a second opening defined therein. A seal is operatively connected to the mask body and adapted for confronting engagement with a surface of a user to form a sealed interface therewith. As discussed above, the seal includes a first portion defined by a gel substance and a second portion associated with the first portion that includes a selectively formable substance adapted to be molded from a first pattern into a second pattern and to retain the second pattern responsive to being so molded.

It is yet another object of the present invention to provide a method of interfacing a patient with an external device using the customizable seal described above. This object is achieved by providing a method that includes the steps of: (1) providing an external device having a seal adapted for confronting engagement with a surface of the patient to form a sealed interface therewith, the seal including a selectively formable portion having a malleable state and a fixed state, (2) causing the formable portion of the seal to be placed in the malleable state, (3) applying the seal to the surface of the patient while the formable portion is in the malleable state so that the formable portion takes on a shape generally conforming to the contour of a portion of the patient underlying the seal, and (4) causing the formable portion to be placed in the fixed state to retain the shape generally conforming to the contour of the portion of the patient underlying the seal.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE INVENTION

Figure 1:
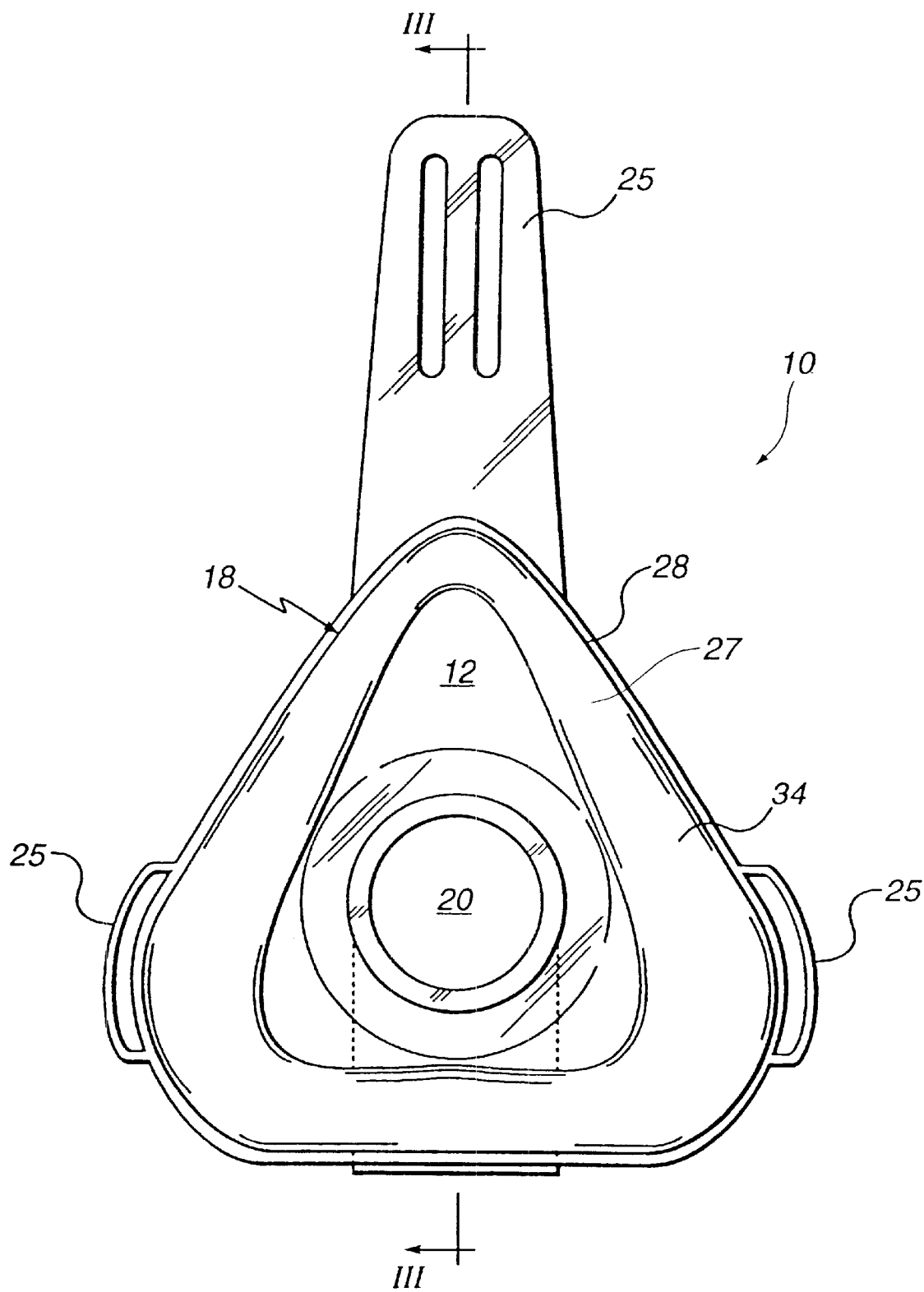
FIG. 1 is a front elevation view of a respiratory mask including a first embodiment of a seal according to the present invention.
Figure 2:
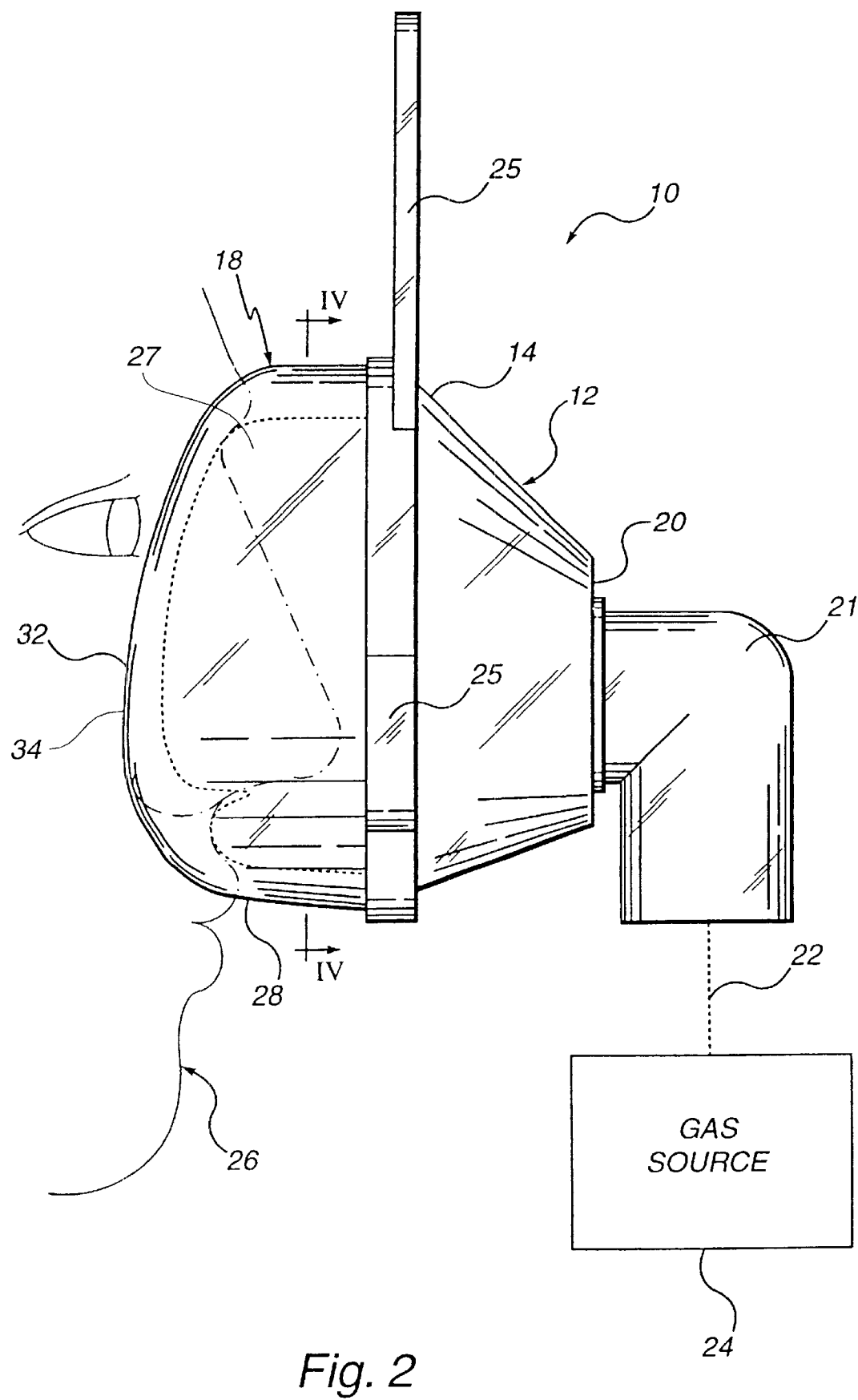
FIG. 2 is a side elevation view of the respiratory mask of FIG. 1 in confronting, sealing engagement with a user's face, the respiratory mask being schematically depicted in communication with a source of respiratory gas.

Referring to FIGS. 1–4, there is generally indicated at 10, a respiratory mask including a shell or body 12 having an open side 14 that defines a generally annular surface 16 to which is sealingly affixed a seal 18 constructed according to a first embodiment of the instant invention. Mask body 12 is preferably, although not necessarily, a generally rigid shell, whereas facial seal 18, in the illustrated embodiment, is a flexible, resilient unitary member that will be described in greater detail hereinafter.

Mask body 12 also defines an opening 20 to which, in the illustrated embodiment, there is attached a fluid coupling device, such as a swivel coupling 21 for carrying fluid, such as a breathing gas, between the chamber within the mask and the external gas source. It is to be understood that the present invention contemplates a variety of fluid coupling devices be attachable, either permanently or selectively, to opening 20 to carry fluid to or from the chamber defined by mask 10. In the illustrated embodiment, opening 20 and intervening coupling 21 connect mask 10 via a conduit, which is represented by dashed line 22, to a source of gas 24, e.g., a blower or other suitable device, for providing a flow of pressurized breathing gas, for example, for administration of the gas to a user 26.

The mask shown is a nasal mask that accommodates the nasal regions of the user's face. It is to be understood, however, that the present invention also contemplates a full face or an oral/nasal mask that accommodates both the mouth and nose of a user or a total face mask that accommodates substantially the entire facial area of the patient. As is conventional, mask body 12 also preferably includes fastening devices, such as tabs 25 or the like, that connect to suitable adjustable retention straps (not illustrated) for retaining the mask with respect to the user's face. Although three such devices are illustrated in the FIGS. 1–4 and are generally arrayed at the corners of mask 10, it is to be understood that other configurations, arrangements, numbers and locations of fastening device can be provided without deviation from the principles of the present invention. Although not illustrated, the present invention contemplates providing one or more exhaust ports or other venting mechanisms at a location or locations, such as in seal 18, mask body 12, conduit 21 or at a junction between these components, to exhaust gas expired by the user to atmosphere.

Seal 18 in the illustrated embodiments includes a solid, yet highly resilient and self-sustaining compressible, generally annular member 27 comprising a peripheral wall portion 28 having a generally annular base or inner end 30 configured so as to substantially match surface 16 of shell 12 to which it is attached. Peripheral wall portion 28 further establishes an outer end 32 generally opposite inner end 30. Outer end 32 defines a generally annular contoured sealing surface 34 adapted for confronting, sealing engagement with a user's face. As will be more fully developed later herein, in the illustrated embodiment, the contour of sealing surface 34 is preformed to closely approximate the surface contour of a user's facial structure, especially in the areas of the bridge of the nose, the cheeks adjacent the nose, the space intermediate the nose and upper lip, and the intervening areas contiguous to these. It can be appreciated that a variety of different contours of sealing surface 34 can be provided, with the user selecting the seal having a contour that most closely matches his or her facial structure, so that the present mask and seal offers the general macro-customized features discussed above.

It is to be understood that the contour of sealing surface 34 can have alternative configurations depending on the type of mask to which the seal is attached. For a full face mask, for example (not illustrated), sealing surface 34 is contoured to accommodate the user's chin in lieu of the area intermediate the nose and upper lip. In either case, variation in the user's facial structure, especially in the area of the bridge of the nose, for example, makes considerable seal flexibility necessary to accommodate the many different facial contours likely to be encountered. This is so despite that fact that a variety of different contours of sealing surface 34 can be provided, bearing in mind that it is only practical to provide a limited number of different contours for sealing surface 34 to facilitate the efficient mass production of seal 18.

Figure 3:
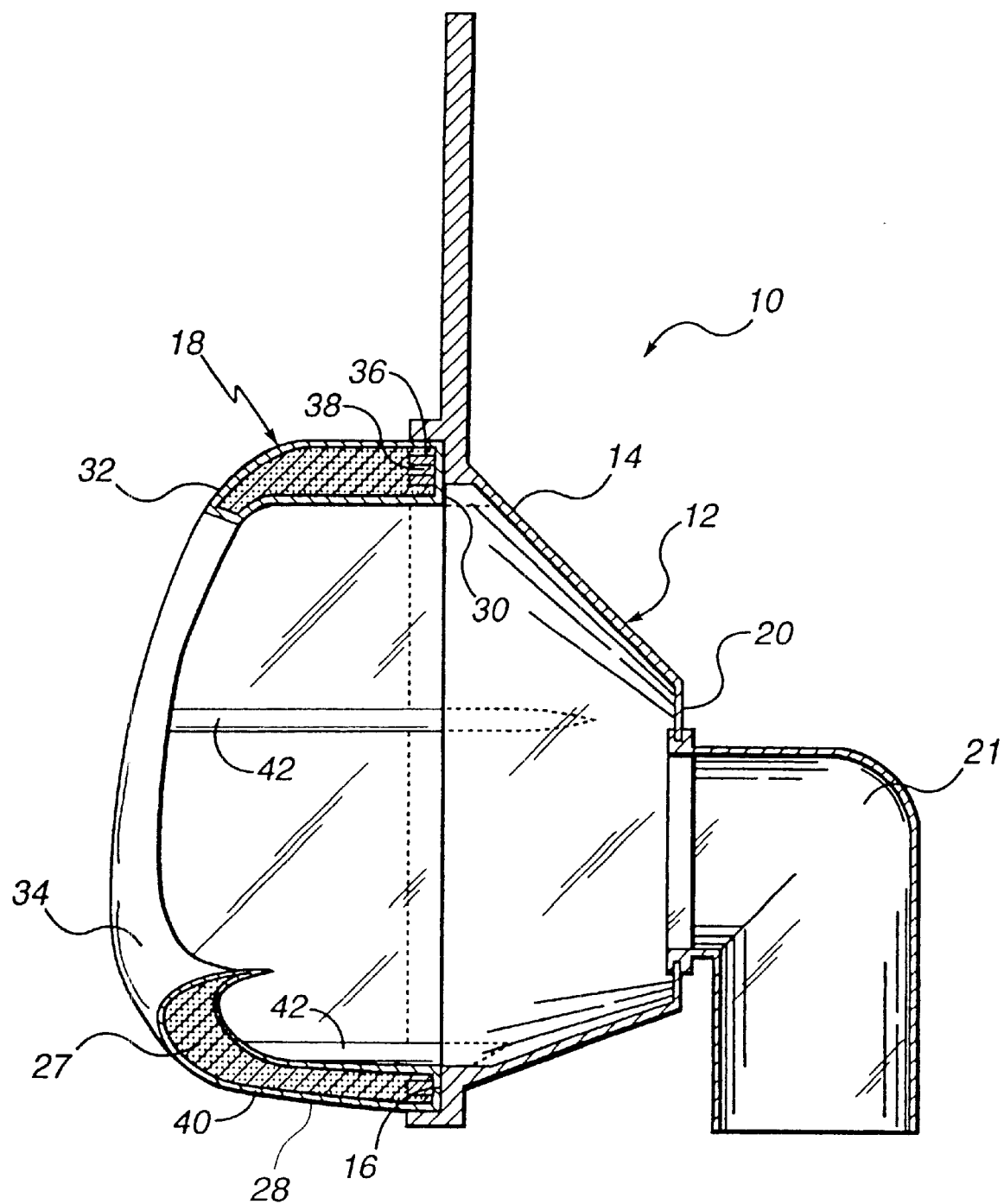
FIG. 3 is a cross-sectional view of the respiratory mask taken along line III—III of FIG. 1.
Figure 4:
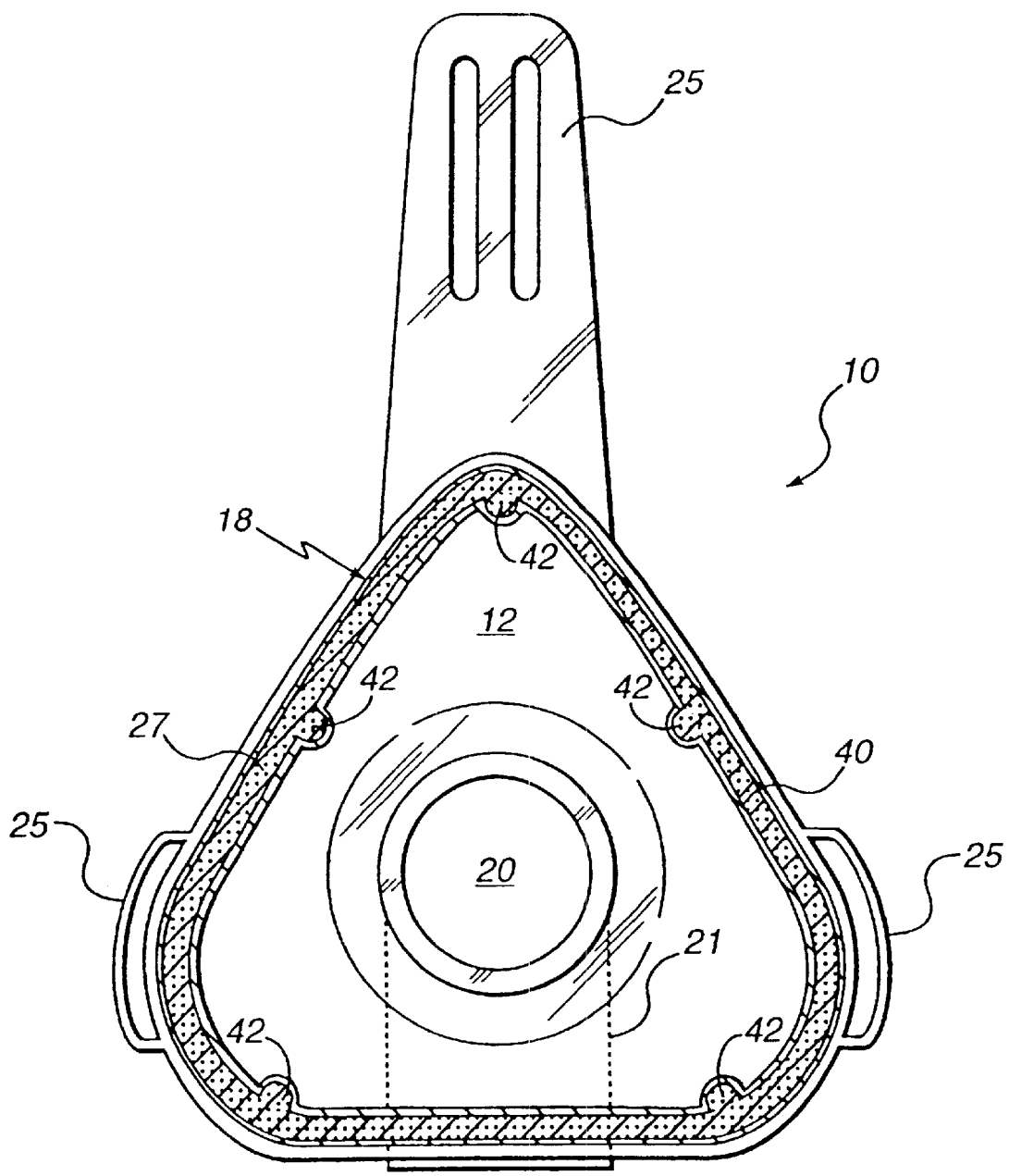
FIG. 4 is a cross-sectional view of the respiratory mask taken along line IV—IV of FIG. 2.

In accordance with the embodiment of the present invention illustrated in FIGS. 3 and 4, the entirety of annular member 27 is formed from a gel substance, such as a viscoelastic polyurethane polymer, possessing resilience or recoil characteristics corresponding substantially to those of human fat tissue. More specifically, seal 18 preferably has a resiliency as defined by durometer measured on the Shore 00 scale, which is used to gauge the resiliency of very soft resilient materials, of about 10 or softer and, most preferably, about 0. Such resiliency corresponds substantially to that of human fat tissue, which also exhibits a durometer reading of 0 on a Shore 00 scale. With respect to the embodiment of seal 18 illustrated in FIGS. 1–4, the durometer of seal 18 corresponds to the resultant durometers of annular member 27 and the later described protective covering (whose durometer is essentially negligible because of the thinness and pliability of the covering). As for the seal illustrated in FIG. 5, wherein the annular member 27 has no protective covering; the durometer of the facial seal is that of the annular member.

Although inherently capable of filling spatial voids, human fat tissue has negligible structural integrity and may not be self-sustaining. Consequently, any seal possessing structural characteristics essentially identical to fat would be impractical from a usage standpoint. That is, if a seal were fabricated from a material structurally indistinguishable from human fat tissue in terms of resiliency, it may tend to sag into an amorphous shape under the influence of gravity and, thus, would not effectively conform to the contours of a user's face even if the headstrap tension was quite high. It will be appreciated, therefore, that a properly designed seal must substantially, but not identically, mimic human fat tissue from a structural, particularly resiliency, perspective. Stated differently, the seal must exhibit some measurable recoil "memory" whereby it is structurally self-sustaining, capable of gently conforming to the topography of a user's face under the influence of low headstrap tensile forces, resistant to distorting gravitational effects and self-restorable to its original configuration when removed from contact with the user's face. It must also be resistant to distortion due to positive gas pressure supplied to the mask.

To simultaneously achieve these and other beneficial properties, annular member 27 according to the present invention is preferably formed from a gel substance that, while virtually indistinguishable from human fat tissue when measured on the Shore 00 scale, exhibits a resiliency or durometer on the Shore 000 scale (which scale is used to measure the resiliency of extremely soft resilient materials) of from about 20 to about 45. By comparison, human fat tissue registers a durometer of about 10 on the Shore 000 scale.

Annular member 27 is fabricated using conventional molding techniques. For example, liquid polyurethane polymer, including any plasticizers and other modifiers necessary to achieve desired finished product properties, is poured or injected into an appropriately configured mold. The polymer is then permitted to cure, either with or without the application of heat depending upon the specific composition and setting characteristics of the polymer, until the product achieves its desired solid gel form.

Because the polymer of the annular member does not have sufficient structural integrity to reliably adhere directly to the body portion 12 of the mask, seal 18 also preferably comprises attachment mechanism 36 that, in one embodiment of the present invention, may be integrally molded into the inner end 30 of the annular member during its formation. Attachment mechanism 36 is desirably constructed as a substantially rigid annular ring having a shape corresponding to that of the inner end 30 and a wall thickness less than or equal to that of the wall thickness of the peripheral wall portion 28. At a minimum, however, attachment mechanism 36 comprises a member less resilient than the gel substance of the annular member. To enhance bonding of attachment mechanism 36 to the annular member 27, the attachment mechanism desirably includes an anchorage device 38. The anchorage device, in the illustrated embodiment, comprises spaced apart formations of the attachment mechanism defining openings or similar structures into or around which the fluid polymer may flow and ultimately cure during formation of the annular member. It is to be understood, however, that a variety of techniques are contemplated from attachment mechanism 36. Any attachment technique, such as screws, tacks, adhesive, or tongue and groove assembly, can be used to secure seal 18 to mask body 12.

In the illustrated embodiment, annular member 27 includes a plurality of integral bosses 42 that are preferably molded into the peripheral wall portion 28 during formation of the annular member and extend from the inner end 30 toward the outer end 32. Bosses 42 provide structural support to the annular member and promote uniform compression of the annular member when such member is in contact with a user's face. In one embodiment of the present invention, the bosses are symmetrically disposed about the peripheral wall portion and preferably correspond in number and location to the anchorage mechanisms 38. As shown in FIG. 3, a presently preferred construction envisions five such bosses 42 corresponding to five anchorage means 38. It is to be understood, however, that the number and positions of bosses 42 can be varied depending on the desired structural characteristics to be achieved.

As previously mentioned, one embodiment of seal 18 contemplates that the annular member 27 be covered by a protective covering 40. The covering increases the durability of the annular member while also permitting easy cleaning of seal 18. Covering 40 must satisfy several physical criteria. It must, inter alia: (1) resist tearing and puncturing, (2) tightly conform to annular member 27 without changing or deforming the contours thereof, (3) be chemically compatible with the annual member, (4) be biocompatible and non-irritating to a user's skin, and (5) be sufficiently thin and supple such that its presence has a negligible impact on the resultant durometer of facial seal 18. In this regard, an exemplary embodiment of the present invention contemplates that covering 40 comprise a thin (approximately 2 to 10 mils thick) flexible plastic film. Urethane has been found to be preferable for this particular purpose as such material meets not only the objectives of the present invention but is also comparatively inexpensive and easy to apply to the surface of annular member 27.

Covering 40 may be applied to the annular member by any suitable process. For instance, liquid urethane may be applied by spraying or dipping and then permitted to cure. Preferably, however, the urethane is prefabricated by vacuum forming so as to produce a skin of controllable and uniform thickness that is subsequently vacuum formed to the annular member using conventional techniques.

Once seal 18 is fully assembled, it is, in one embodiment of the present invention, attached to mask body 12 by coating inner end 30 of the facial seal and/or annular seating surface 16 of the mask body 12 with a suitable adhesive and then pressing inner end 30 into abutment with seating surface 16 whereupon the adhesive is allowed to cure.

Figure 5:
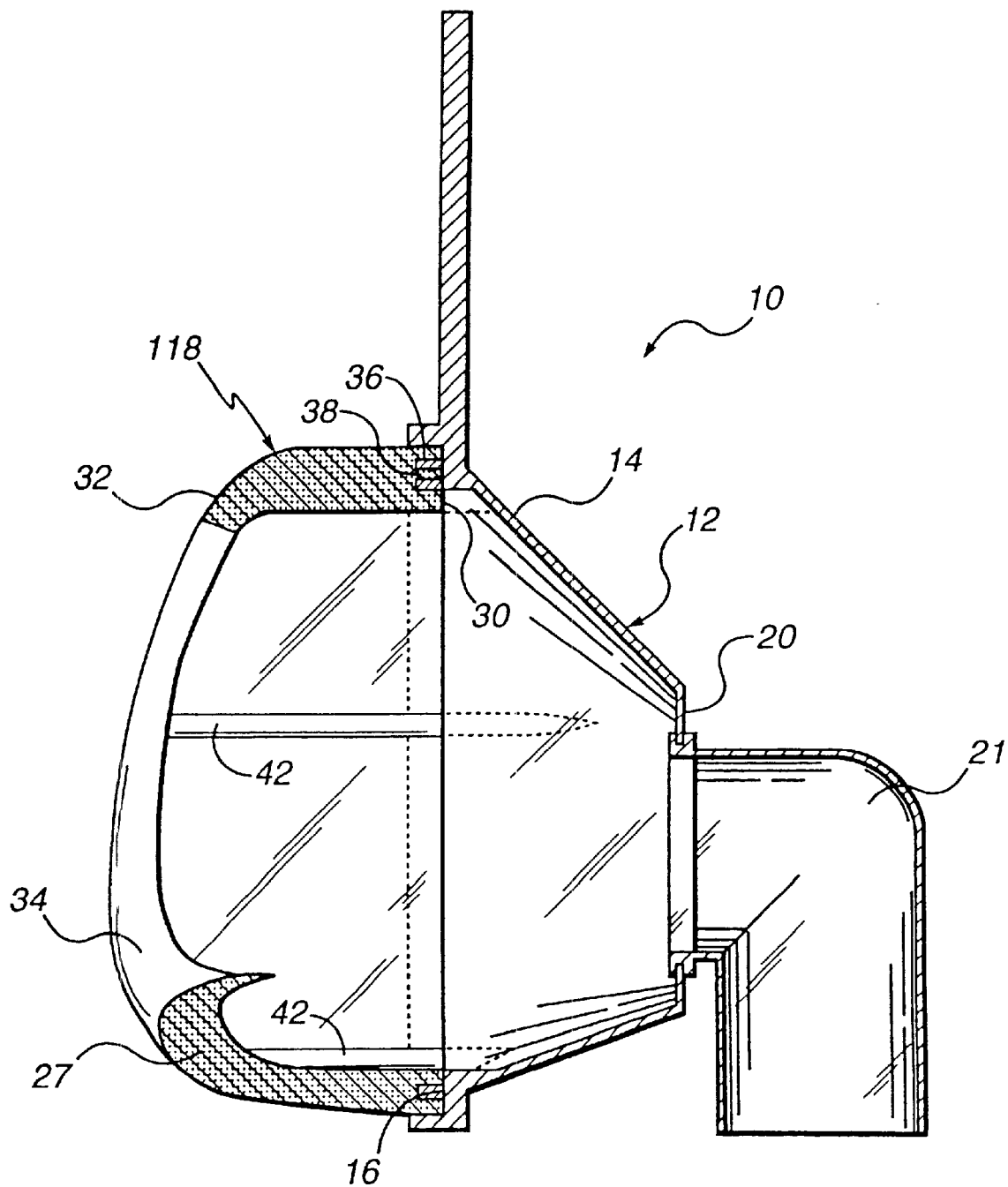
FIG. 5 is an elevational cross-sectional view of a respiratory mask similar to the view illustrated in FIG. 3 illustrating a seal according to another embodiment of the present invention.

FIG. 5 illustrates a further preferred embodiment of the seal of the present invention, which is identified herein by reference numeral 118. Seal 118 differs from seal 18 essentially in that the annular member 27 thereof has no protective covering on its outer surface. In all other material respects, seal 118 is constructed and functions substantially identically to seal 18.

When manufactured according to a preferred embodiment of the present invention, the exposed surface of annular member 27 is tacky. As such, the inherent tackiness of contoured sealing surface 34 of the annular member may, thus, be used to the user's advantage by enhancing adhesion of the seal to the user's face. In the alternative, if tackiness is not desired, the surface of annular member 27 of seal 118 may be covered with a coating of powdered talc, silicone or similar biocompatible material.

As presently contemplated, the wall thickness of peripheral wall portion 28 of annular seal member 27 of seals 18 and 118, excluding bosses 42, preferably ranges from about 0.2 to 0.3 inches. The weight of the seals 18 and 118, depending on the size of mask bodies 12 with which they are used, ranges from about 1 to 2 ounces, a weight that has been discovered to be virtually unnoticeable to patients who have worn masks constructed according to the present invention in clinical tests. Furthermore, the fat-like resiliency qualities of the gel substance that forms annular member 27 creates in the wearer a comparatively cool and natural tactile sensation when the facial seal is in contact with the user's face. Also, much like human fat tissue performs, seals 18 and 118 effectively fill gaps and mold to the user's facial topography thereby minimizing leakage of gas supplied to the mask. Thus, seals 18 and 118 provide the beneficial aspects of micro-customization as discussed above. Indeed, experimental testing has shown that respiratory masks fitted with facial seals in accordance with the present invention exhibit minimal gas leaks with headstrap tensile forces of 3 pounds or less, a value substantially less than related masks presently known in the art. The facial seals described herein thus enable respiratory masks to be worn by users for prolonged periods with little or no measurable discomfort. This phenomenon is especially important to users who must wear respiratory masks for extended periods, such as patients undergoing respiratory therapy. Such individuals find that because of the comfort afforded by the facial seals 18, 118, their compliance with the respiratory treatment increases and the therapeutic benefits of the treatment are more fully realized.

As an alternative to the embodiments discussed above, it is also contemplated that a respiratory mask of the present invention may be constructed as a one-piece member rather than as a separate seal joined to a mask body. In such case, the respiratory mask may be fabricated as a unitary member formed from substances of increasingly softer durometers, as considered in a direction from that portion of the mask corresponding to the mask body toward that portion corresponding to the facial seal, such that the softest materials, comprising the previously discussed gel substance and possessing the resiliency characteristics described hereinabove, constitute the seal or face-contacting portion of the annular member.

As yet another alternative embodiment, the present invention also contemplates that annular member 27, rather than the entire mask, can be defined by substances of increasingly softer durometers in a direction toward sealing surface 34, such that the softest materials, comprising the previously discussed gel substance and possessing the resiliency characteristics described hereinabove, would constitute the seal or face-contacting portion of the annular member, i.e., the portions of seal 18 at sealing surface 34.

Figure 6:
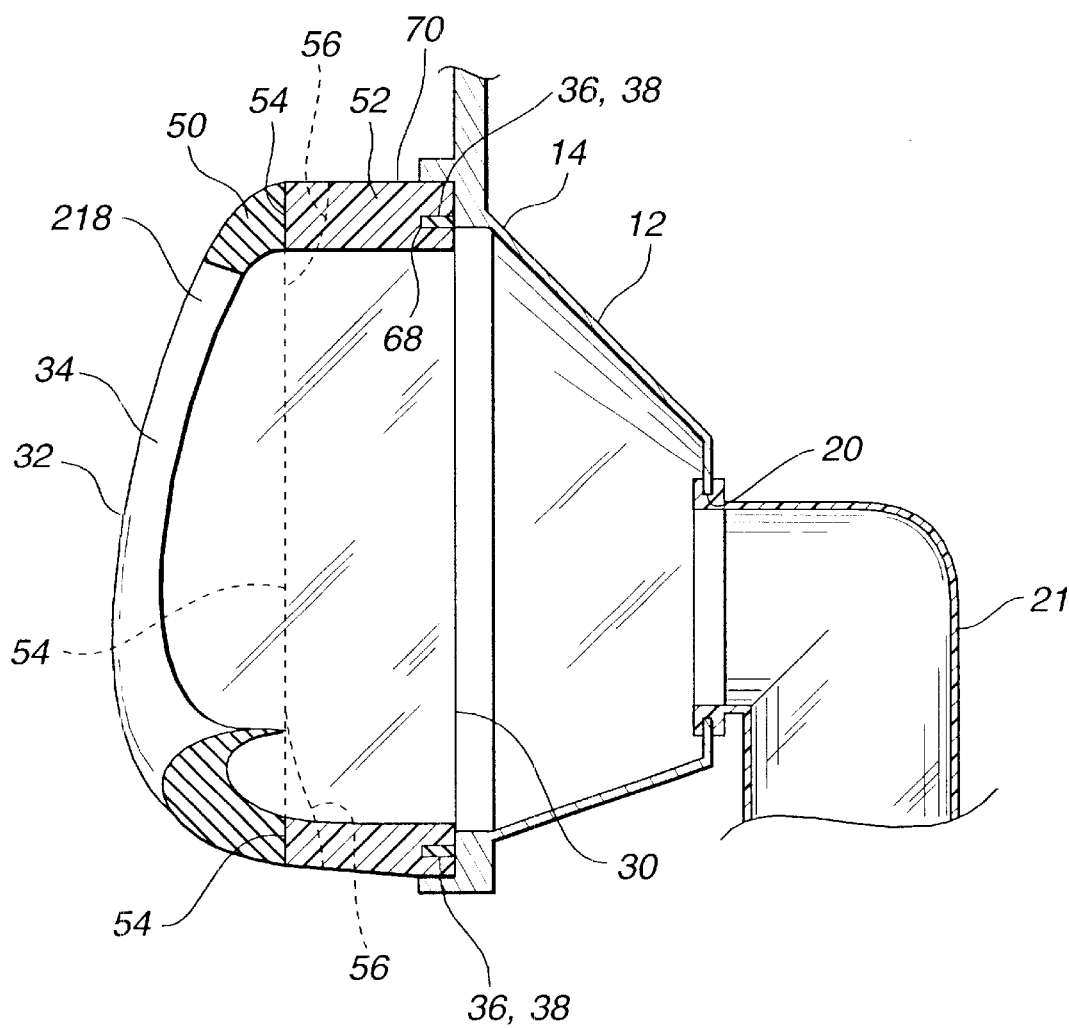
FIG. 6 is a cross-sectional view of a respiratory mask similar to the view illustrated in FIG. 3 illustrating a seal according to a still further embodiment of the present invention.

A further embodiment of a seal of the present invention is illustrated in FIG. 6. The primary difference between the seal of this embodiment, identified by numeral 218, and seals 18 and 118 in the previous embodiments, is that seal 218 includes a first portion 50 defined by the gel substance discussed above and a second portion 52 defined by a selectively formable substance so that the general shape of seal 218 can be customized to enable seal 218 to fit more comfortably on the patient. The remaining portions of the mask illustrated in FIG. 6 are identical to the associated portions in the previous embodiments.

The selectively formable substance in second portion 52 of seal 218 is capable of being placed in a malleable state so that it molds from a first pattern into a second pattern. The formable substance is also capable of being placed in a fixed state so that it retains the second pattern after being so molded. Dashed line 54 in FIG. 6 represents the interface between first portion 50 and second portion 52 when second portion 52 is in its original, first pattern, i.e., prior to being molded to match the contours of the patient. Dashed line 56, on the other hand, represents the interface between first portion 50 and second portion 52 once second portion 52 has been molded into its second pattern to match the contours of the patient. It can be appreciated that second portion 52, in the embodiment illustrated in FIG. 6, upon being molded into its second pattern, has decreased the distance between inner end 30 and the interface 54, 56 between first portion 50 and second portion 52 at the top and bottom of the seal as a result of being so molded. This may occur, for example, due to the protrusion of the bridge of the nose and the chin.

In an exemplary embodiment of the present invention, the formable substance in second portion 52 of seal 218 is heat activated so that it transitions from the fixed state to the malleable state upon being heated to a certain level. It also transitions from the malleable state to the fixed state upon being cooled to certain level. In one embodiment of the present invention, the formable substance defining second portion 52 is a combination of the above-described gel substance and a stiffening agent, such as ethyl vinyl acetate. Although a range of mixture ratios are possible to achieve a variety of stiffnesses for second portion 52, in a preferred embodiment of the present invention, the second portion is a uniform mixture of approximately 60% gel substance and 40% stiffening agent.

This embodiment of the present invention provides a customizable seal for interfacing an external device, such as the mask illustrated in FIG. 6, with a portion of the patient, such as the area surrounding the patient's nose or the area surrounding the nose and mouth. More specifically, by providing a formable substance as second portion 52 of seal 218, the seal can be macro-customized to match the general contours of the patient, such as the bone structure underlying the portions of the patient's face over which the mask is to be placed. In addition, first portion 50 of seal 218, being a gel substance as described above with respect to FIGS. 1–5, provides the beneficial effects of micro-customization in that the gel readily conforms to the external features of the patient's face and does not suffer from the disadvantages of micro-customization because the gel need not be patterned to match the specific features of the user. Instead, the consistency of the gel allows the first portion to fill in the gaps on the surface of the user once the seal is applied to the user. Thus, a single seal 218 provides the benefits of micro-customization and macro-customization.

Furthermore, the formable substance in second portion 52 can be reshaped, as needed, merely by causing the formable substance to transition again to the malleable state, which, in the above embodiment, is accomplished by reheating the second portion. Thus, seal 218 can be re-customized if, for example, the patient is unsatisfied with a previous attempt to customize the seal. Still further, because the gel substance of first portion 50 provides the effect of micro-customization without having to perform the time-consuming and typically permanent micro-customization process discussed above and because the second portion can be customized to match the general contours of a patient, a commonly configured seal having first and second portions 50 and 52 can be adapted for use with a wide variety of patients, thereby maximizing the efficiency of the manufacturing process. This feature also makes it possible to minimize the number of different off-the-shelf variations in the seal shape and size that must be made available in order to provide a seal suitable for each patient from a group of patients having a wide range of different physical characteristics.

The process by which seal 218 is customized to match, in general, the facial features of the patient begins with selecting a seal that generally matches the user. For example, the size of seal 218 must be generally compatible with the size of the area of the user that the seal must cover. This is accomplished, for example, by making a variety of sizes of seal 218 available to the user. After an appropriately sized seal is selected, the formable portion of the seal 218 is caused to transition to a malleable state. This is accomplished, according to a preferred embodiment of the present invention, by heating at least second portion 52 of seal 218 to a temperature sufficient to activate the thermally activated material (stiffening agent) to cause it to transition to the malleable state.

Heating the second portion of the seal can be performed in a variety of ways. In a preferred embodiment of the present invention, seal 218 is placed in a heated liquid, such as boiling water, for a period of time sufficient to cause second portion 52 to transition to the malleable state. Typically, four (4) or more minutes is sufficient. Heating the second portion can also be performed, for example, by using an oven, microwaving the seal, or applying a heat source to the seal.

After the seal has been heated to a degree sufficient to cause the formable portion to transition to the malleable state, the exposed portion of seal 218, preferably the patient contacting portion 32, is cooled so that the seal can be applied to a human without substantial discomfort or damage to the patient's tissue. Cooling can be accomplished, for example, by removing the seal from the heated liquid and allowing it to cool in the ambient air or in a chilled chamber, such as a refrigerator. However, in a preferred embodiment, cooling is accomplished by quenching, which involves placing the seal for a brief period of time, which is typically shorter than the period of time it is placed in the boiling water, in a liquid, such as water, having a temperature less than that used to cause the seal to transition to the malleable state.

The relatively high thermal resistance of the seal prevents the brief cooling of its exterior, such as from quenching, from significantly affecting the malleability of the second portion. That is, the degree of cooling that takes place in the cooling step should not be sufficient to cause the formable portion of the seal to transition or begin to transition to the fixed state due to the ability of the interior of the seal to retain heat and due to the relatively short quenching time. Quenching can be done to the entire seal or, preferably, quenching is limited to distal surface 32 that contacts the user. It can be appreciated that the quenching time will vary from patient to patient depending on the patient's sensitivity to heat. It will also depend on the location of the body where the seal is being applied, because some parts of the body are more sensitive to heat than others.

Once the exterior of the seal has been reduced to a temperature that can be tolerated by the user, the seal is applied to the surface of the user or vice versa. This can be done by manually holding the seal against the user or, in the case where the seal is part of a mask, by strapping the mask on the user. Preferably, a sufficient force is applied on the seal so as to cause second portion 52 to take on a shape generally conforming to contours of a portion of the patient underlying the seal. As the second portion of the seal cools while the seal is applied to the user, the second portion transitions from the malleable state to the fixed state, thereby retaining a shape generally conforming to the contour of the portion of the user underlying the seal. As noted above, dashed line 56 in FIG. 6 illustrates an example of the shape of second portion 52 following the above customization procedure. In this manner, the formable second portion of the seal provides a degree of macro-customization so that the seal conforms more closely to the general contours of the user, thereby reducing pressure points and enhancing the comfort of the external device to which the seal is attached.

The above steps of causing the seal to be placed in a malleable state, placing the seal on the user to cause it to assume a pattern corresponding to the general contour of the user, and causing the seal to be placed in a fixed state after it has assumed the new pattern can be repeated as necessary to reshape the seal. Thus, the present invention provides a very high degree of flexibility in matching the shape of the seal to the structure of the user. Providing a repeatable customization also makes it possible for the same seal to be used on a variety of patients, assuming, of course, that the appropriate cleaning and/or sterilization is done. Also, the same seal can be used on the same patient even if the patient's general facial contours change.

In the embodiment of seal 218 illustrated in FIG. 6, first portion 50 and second portion 52 are generally integral with one another with the junction between the two portions being defined by a generally planar interface 54. This is accomplished, for example, by providing the gel substance defining first portion 50 in a mold having a shape corresponding to seal 218, and, thereafter, providing the formable substance defining the second portion 52 to the mold on top of the first portion. The molding process can be performed such that two layers fuse together or the manufacturing process can include affixing the two layers to one another through the use of a bonding mechanism, such as an adhesive.

Figure 7:
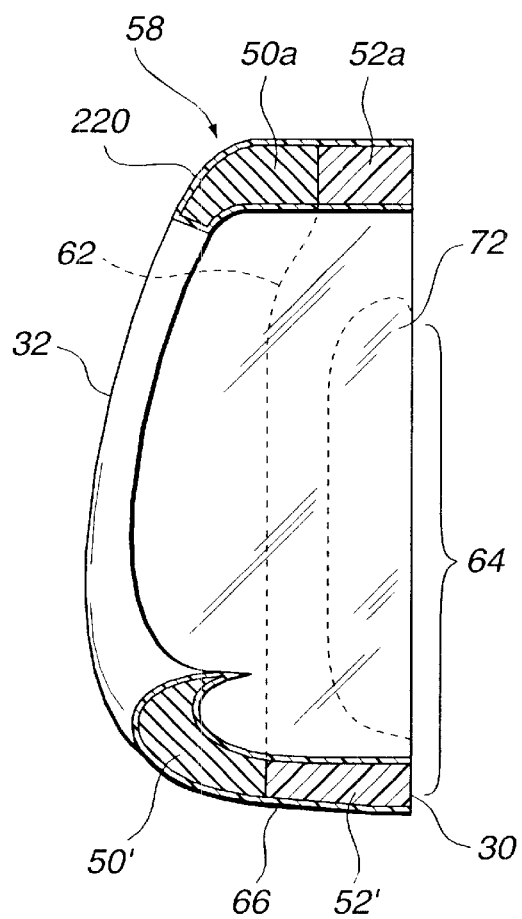
FIGS. 7 and 8 are cross-sectional views of a seal according to other embodiments of the present invention.

Although FIG. 6 illustrates a substantially planar interface between first portion 50 and second portion 52, it is to be understood, however, that the interface between first portion 50 and second portion 52 need not be planar. On the contrary, the interface between first portion 50 and second portion 52 can vary in three dimensions depending on the desired structural characteristics of the seal. FIG. 7, for example, illustrates a seal 220 in which an interface 62 between first portion 50a and a second portion 52a is generally planar throughout an area 64. However, at area 58, the distance from interface 62 to inner end 30 decreases so that more of first portion 50a, which contains only the gel substance, is provided next to the bridge of the nose.

FIG. 7, like FIG. 3, also illustrates a thin membrane 66 protective covering an exposed surface of seal 220. In FIG. 7, membrane 66 overlies both first portion 50a and second portion 52a. It is to be understood, however, the membrane 66 can be provided over only one of these portions or over selected areas of the seal depending on the characteristic desired by the user.

Although FIG. 6 illustrates a relatively distinct separation between first portion 50 and second portion 52, it is to be understood, however, that there need not be such a distinct separation of these portions. On the contrary, seal 218 can be constructed and arranged so that the mixture ratio of gel to stiffening agent gradually changes in the direction from inner end 30 to outer end 32. For example, in one embodiment of the present invention, the mixture ratio of gel to stiffening agent increases in the direction from inner end 30 to outer end 32 so that first portion 50 of seal 218, which is substantially 100% gel substance, is disposed at outer end 32, with no specifically defined transition from second portion 52, which is proximate to inner end 30, to first portion 50.

Providing a seal in which the mixture ratio of gel to stiffening agent gradually changes in the direction from inner end 30 to outer end 32 can be accomplished, for example, by filling a mold entirely with the formable substance, which is a combination of the above-described gel substance and a stiffening agent at a certain mixture ratio. The separate layers, or, more precisely, the change in mixture ratio from inner end 30 to outer end 32, is achieved by placing the mold on a centrifuge so that the heavier stiffening agent is drawn toward inner end 30. The change in mixture ratio in the direction from inner end 30 to outer end 32 is controlled based on the time spent on the centrifuge and/or the speed of the centrifuge.

The present invention also contemplates that the mixture ratio can vary in three dimensions. For example, the mixture ratio of gel to stiffening agent can be lower near inside surface 68 than near outer surface 70 or vice versa. Also, the rate of change in the mixture ratio from one portion to another in seal 218 need not be constant, i.e., linear. Instead, the rate of change in mixture ratios can vary depending on the desired characteristics for seal 218. Furthermore, the physical location of the areas of changing mixture ratios in the seal can vary depending on the needs of the user.

For example, second portion 50a of the seal corresponding to the bridge of the nose, identified as area 58 in FIG. 7, can be a mixture whose gel to stiffening agent mixture ratio is a 2:1 throughout the entire second portion thereof, and, thereafter, changes abruptly to the first portion having the gel substance alone. However, in another part of the seal, such as at a portion 72 extending between the sides of the nose and the sides of the mouth, the mixture ratio of the second portion can range from approximately 40% gel substance and 60% stiffening agent at inner end 30 to approximately 60% gel substance and 40% stiffening agent at the junction between first portion 50a and second portion 52a, at which point the composition of the seal is substantially 100% gel substance through first portion 50a, i.e., from interface 62 to outer end 32. In short, the present invention contemplates that the mixture ratio, the rate of change of the mixture ratio, and the location of the mixture ratio can vary in three dimensions throughout the seal so long as the seal remains capable of performing the micro-customization and macro-customization functions discussed above.

Furthermore, the present invention contemplates that there may be multiple layers of first portion 50 and/or second portion 52 defining the seal. For example, in an exemplary, non-illustrated embodiment of the present invention, a first layer of formable substance (second portion 52) is disposed at or near inner end 30 followed by a second layer of gel substance (first portion 50). A third layer of formable substance (second portion 52) is disposed on the second layer, and a fourth layer of gel substance (first portion 50) is disposed on the third layer and defines outer end 32.

Figure 8:
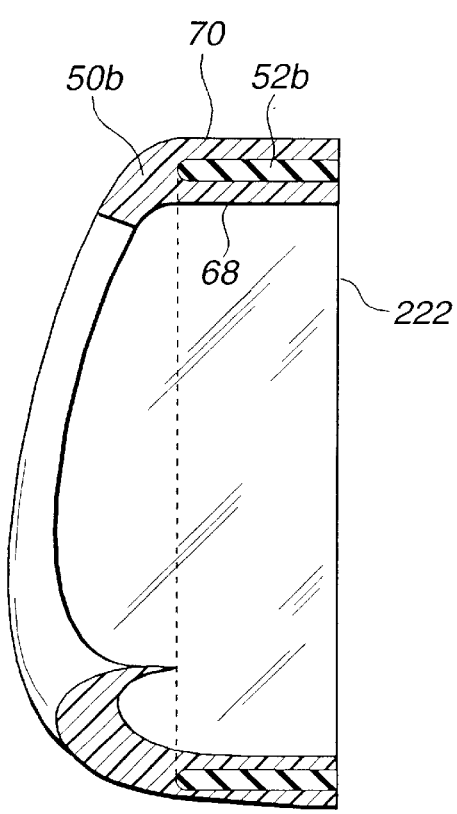

FIG. 8 illustrates another example of a seal 222 having a first portion 50b and a selectively formable second portion 52b. In this embodiment, second portion 52b is disposed within the gel substance of the first portion such that the gel substance having no stiffening agent is between second portion 52b and inside surface 68 and between the second portion and outside surface 70. This embodiment simplifies the manufacturing process in that second portion 52b is inserted into the first portion during the molding process, thereby eliminating the difficult process of forming multiple layers of differing substances adjacent one another during the manufacturing process. In addition, the shape of the insert for second portion 52b can be easily controlled to simplify the manner in which the shape of the formable portion, second portion 52b, is determined. Furthermore, providing second portion 52b as an insert into first portion 50b maximizes the surface area and, hence, area of contact between these two portions, thereby increasing the bonding strength therebetween.

Figure 9:
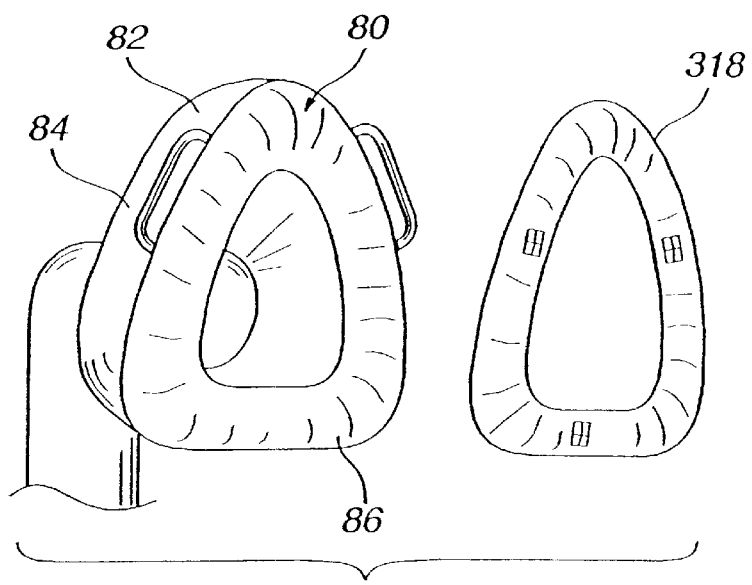
FIG. 9 is an exploded view of a respiratory mask and seal according to a further embodiment of the present invention.

Referring again to FIG. 6, as with the embodiment illustrated in FIGS. 1–5, an attaching mechanism 36, which, in a preferred embodiment of the present invention includes an anchorage device 38, attaches the seal, such as seal 218. 220 or 222, to an external member. In the illustrated embodiment, the external member is mask body 12. It is to be understood, however, that the seals of the present invention, i.e., seals 18, 118, 218, 220 and 222, need not be relatively permanently affixed to the external member, such as the mask body. Quite the contrary, the seals of the present invention can be associated with the external member without any significant, i.e., relatively permanent, attachment between the seal and the external member. For example, FIG. 9 illustrates an embodiment of the present invention in which seal 318 is an annular member that is applied to an exposed surface 80 of a mask 82, which is any conventional respiratory mask, and includes a mask body 84 and a cushion 86. Seal 318 has the characteristics of any of the seals discussed above.

In one embodiment of the present invention, the exposed surface of seal 318 in FIG. 9 is tacky, and the inherent tackiness of the seal facilitates the attachment of the seal to exposed surface 80 of cushion 86 and to the user. The present invention contemplates, however, that at least a portion of seal 318 can be provided with a membrane, such as membrane 66, or with a coating of powdered talc, silicone or similar biocompatible material. If desired, a suitable bonding agent can be employed to augment or provide an attaching mechanism for affixing seal 318 to the mask or to the patient.

Figure 10:
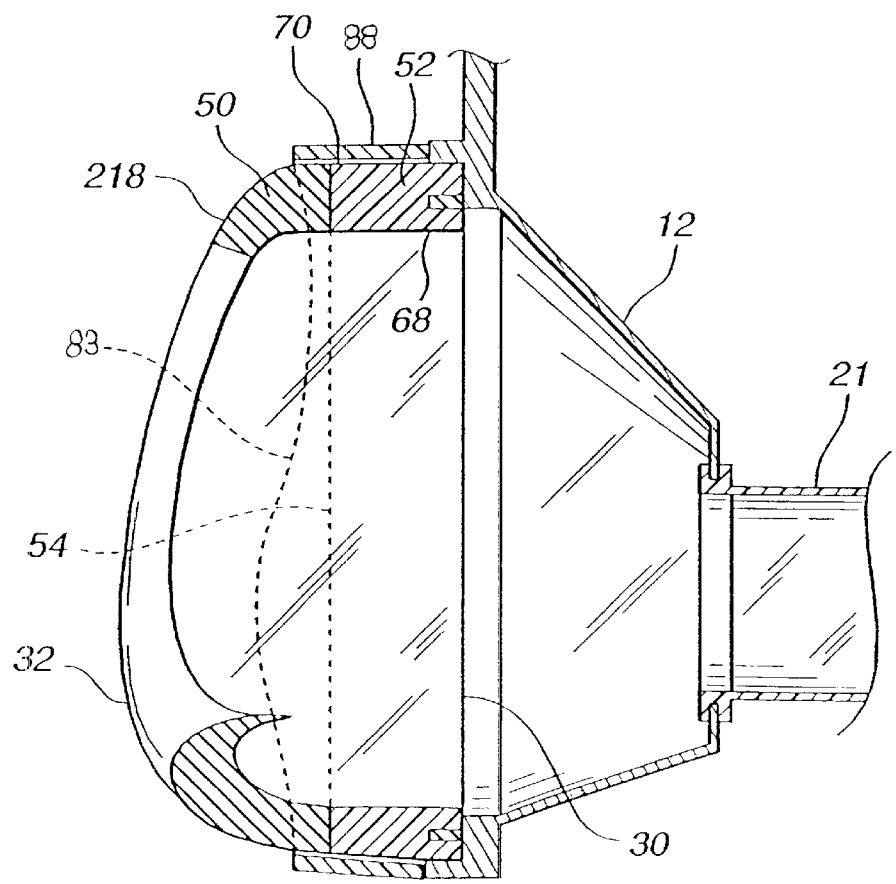
FIG. 10 is a cross-sectional view of a respiratory mask similar to the view illustrated in FIG. 3 illustrating a retaining member used in customizing the seal to the patient in a further embodiment of the present invention.
Figure 11:
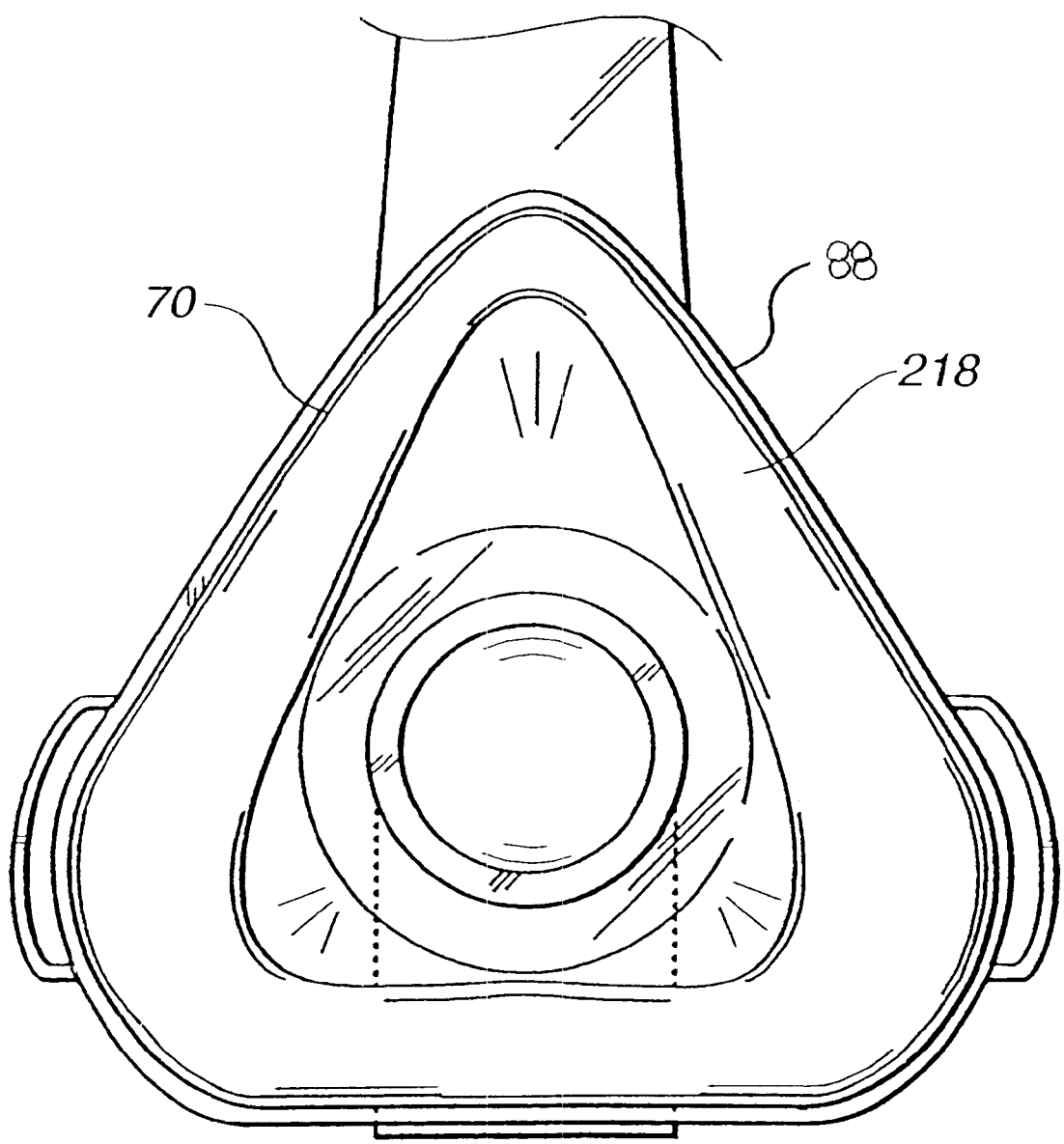
FIG. 11 is a front elevation view of the respiratory mask and retaining member shown in FIG. 9.

FIGS. 10 and 11 illustrate a further embodiment of a step for use in the method by which the seal of the present invention is customized to match the general features of the user. In this embodiment, a retaining member 88 is provided proximate to seal 218 to prevent movement of the seal during the process in which the second portion 52 changes shape from the first pattern to the second pattern. Although seal 218 is illustrated in FIGS. 10 and 11, it is to be understood that the use of a retaining member during this stage of the interfacing process is not limited to this seal. On the contrary, retaining member 88 can be used in conjunction with any seal having a portion that is molded from a first pattern to a second pattern, such as seal 220 or 222, to assist in retaining the shape of the seal as it is being applied to the patient to customize to the physical features of that patient. The present invention also contemplates using a retaining member in a finished seal of any of the type discussed above to augment the support of the seal in use, i.e., to increase the stiffness of the seal.

In the embodiment illustrated in FIGS. 10 and 11, retaining member 88 is provided proximate to seal 218 either before seal 218 is heated or after second portion 52 of seal 218 has been heated to a level sufficient to cause the second portion to transition from the fixed state to the malleable state. Retaining member 88, being disposed proximate to the outer surface 70 periphery of seal 218, minimizes outward expansion of seal 218 so that the act of compressing the seal on the user does not tend to flatten the seal, but enhances the ability of second portion 52 to mold to the general shape of the patient.

It is to be understood that the retaining member can be provided at a variety of locations, or a plurality of locations, depending on how the user wants to support the seal, either during the customization process or while the seal is in use. For example, the retaining member may be provided proximate to the inner surface 68 and/or outer surface 70. As illustrated by hidden line 83 in FIG. 10, which illustrates the distal surface of retaining member 88, the retaining member can have a variety of shapes depending on the pattern of support to be provided. It is to be further understood that retaining member 88 need not be an annular member, but may be a portion thereof and attachable to mask body 12, for example, to provide the desired support function.

While the presently preferred embodiments of the seal, and, in particular, the customizable seal, have been discussed above with respect to its use on a respiratory facial mask as the external member, it is to be understood that there are a wide variety of alternative uses for the seal of the present invention. For example, the present invention contemplates using a seal having the features described above in conjunction with a mask that is worn to protect the user's eye, such as goggles worn by a swimmer. The present invention also contemplates that the external member is an earphone or any such device that surrounds the user's ear. The external member can also be a headpiece or helmet, with the seal providing a comfortable and customizable interface between the user and the headpiece and/or helmet or helmet straps. In addition, the external member can be a garment, such as a glove or boot, with the seal being used at the cuff of the glove, for example, to provide a seal at the user's wrist, hand or arm. The present invention also contemplates that the external member be a protective item, such as a shoulder pad, or a medical item, such as a cast or brace, worn by the user. In addition, the present invention contemplates providing the seal, and, in particular, the customizable seal in conjunction with larger external devices, such as a chair or bed, with the seal serving as a seat cushion or as an insole for a shoe, for example.

It is also not necessary for the seal of the present invention to be an annular member as generally shown in the figures. On the contrary, the seal can be formed in a variety of shapes depending on the intended use. For example, the seals of the present invention can be provided at various locations on a firearm, such as at the stock and/or butt, to provide a comfortable and customizable interface with the user. In the office, the seal can be provided, for example, on a telephone headset, a keyboard wrist support/rest pad, a mouse, and even as a grip on a writing instrument to provide a comfortable and customizable interface with the user. The seal of the present invention has a wide variety of uses in the medical devices. For example, the seal can be provided at the earpiece of a stethoscope, in which case, it is particularly advantageous to provide a customizable seal so that the earpiece can be tailored to fit in the ear of each individual user.

It should be further understood that the above described alternative embodiments of the present invention are not intended to be an exhaustive list of all of the possible uses for the seal of the present invention. In general, the seal of the present invention can be used in any situation where there is an interface between a user and an external device. It should be noted that the term "seal" is intended to encompass any interface between a patient and an external device. The term "seal" should not be construed narrowly, for example, to cover only those situations where the seal prevents foreign matter, such as water or gas, from passing to the user, e.g., a water-tight seal or an air-tight seal. It is not necessary in all embodiments of the present invention that the seal prevent matter from passing to the user. For example, if the seal of the present invention is used as an earpiece for a telephone receiver, it is not necessary that the interface between the receiver and the user provided by the seal be airtight or watertight. All that is required is that the seal of the present invention provide a cushioned and customizable interface between the user and the external device, such as the telephone receiver.

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. A seal adapted for confronting engagement with a surface of a user to form an interface therewith, said seal comprising:
   a first portion defined by a gel substance; and
   a second portion associated with said first portion and including a selectively formable substance adapted to be molded by a compressive force acting on the second portion from a first pattern into a second pattern and to retain said second pattern responsive to being so molded and even after the compressive force is removed.

2. A seal according to claim 1, wherein said selectively formable substance includes a combination of said gel substance and a stiffening agent.

3. A seal according to claim 2, wherein said stiffening agent is ethyl vinyl acetate.

4. A seal according to claim 2, wherein said combination of said gel substance and said stiffening agent is a uniform mixture of approximately 60% said gel substance and 40% said stiffening agent.

5. A seal according to claim 2, wherein a mixture ratio of said gel substance to said stiffening agent gradually changes over a dimension of said seal so that said first portion is disposed at a surface of said seal.

6. A seal according to claim 1, wherein said gel substance has a resiliency defined as a Shore 00 durometer of less than about 10.

7. A seal according to claim 1, wherein said gel substance has a resiliency defined as a Shore 000 durometer of about 20 to about 45.

8. A seal according to claim 1, wherein said first pattern includes a generally planar interface between said first portion and said second portion.

9. A seal according to claim 1, further comprising an attaching mechanism associated with said second portion at a side thereof opposite a side adjacent said first portion, said attaching mechanism adapted to attach said second portion to an external member.

10. A seal according to claim 1, further comprising a protective covering over an exposed portion of at least one of said first portion and said second portion.

11. A seal according to claim 1, wherein said second portion is substantially integral with said first portion to define said seal as a unitary member.

12. A respiratory mask comprising:
    a mask body having a first opening and a second opening defined therein; and
    a seal operatively connected to said mask body at said first opening and adapted for confronting engagement with a surface of a user to form a sealed interface therewith, said seal comprising:
       a first portion defined by a gel substance, and
       a second portion substantially integrally associated with said first portion and including a selectively formable substance adapted to be molded by a compressive force acting on the second portion from a first pattern into a second pattern and to retain said second pattern responsive to being so molded and even after the compressive force is removed.

13. A respiratory mask according to claim 12, wherein said selectively formable substance includes a combination of said gel substance and a stiffening agent.

14. A respiratory mask according to claim 13, wherein said stiffening agent is ethyl vinyl acetate.

15. A respiratory mask according to claim 13, wherein said combination of said gel substance and said stiffening agent is a uniform mixture of approximately 60% said gel substance and 40% said stiffening agent.

16. A respiratory mask according to claim 13, wherein a mixture ratio of said gel substance to said stiffening agent gradually changes over a dimension of said seal so that said first portion is disposed at a surface of said seal.

17. A respiratory mask according to claim 12, wherein said gel substance has a resiliency defined as a Shore 00 durometer of less than about 10.

18. A respiratory mask according to claim 12, wherein said gel substance has a resiliency defined as a Shore 000 durometer of about 20 to about 45.

19. A respiratory mask according to claim 12, wherein said first pattern includes a generally planar interface between said first portion and said second portion.

20. A respiratory mask according to claim 12, further comprising a protective covering over an exposed portion of at least one of said first portion and said second portion.

21. A respiratory mask according to claim 12, wherein said second portion is substantially integral with said first portion to define said seal as a unitary member.

22. A respiratory mask according to claim 12, wherein said second opening is generally opposite said first opening and provides an interconnection between said mask body and an external member.

* * * * *